US006871094B1

(12) United States Patent
Allen et al.

(10) Patent No.: US 6,871,094 B1
(45) Date of Patent: Mar. 22, 2005

(54) APPARATUS FOR DETERMINING WHEN A PATIENT IS SUSCEPTIBLE TO DEFIBRILLATION

(75) Inventors: James Allen, Muckamore (GB); Johnny Houston Anderson, Holywood (GB)

(73) Assignee: Heartsine Technologies Limited, Belfast (GB)

(*) Notice: Subject to any disclaimer, the term of this patent is extended or adjusted under 35 U.S.C. 154(b) by 0 days.

(21) Appl. No.: 09/936,001

(22) PCT Filed: Feb. 8, 2000

(86) PCT No.: PCT/IB00/00205

§ 371 (c)(1),
(2), (4) Date: Feb. 20, 2002

(87) PCT Pub. No.: WO00/47279

PCT Pub. Date: Aug. 17, 2000

(30) Foreign Application Priority Data

Feb. 8, 1999 (IE) .............................................. S990090

(51) Int. Cl.[7] .................................................. A61N 1/39
(52) U.S. Cl. .......................................... 607/5; 600/518
(58) Field of Search .............................. 607/2, 4, 5, 6, 607/7, 8; 600/518

(56) References Cited

U.S. PATENT DOCUMENTS

| 4,919,144 | A | * | 4/1990 | Vandehey | .................... 600/518 |
|---|---|---|---|---|---|
| 5,257,621 | A | * | 11/1993 | Bardy et al. | .................... 607/5 |
| 5,312,441 | A | * | 5/1994 | Mader et al. | .................... 607/5 |
| 5,507,778 | A | * | 4/1996 | Freeman | ........................ 607/5 |
| 5,607,454 | A | * | 3/1997 | Cameron et al. | ............... 607/5 |
| 5,632,766 | A | * | 5/1997 | Hsu et al. | ...................... 607/5 |
| 5,718,242 | A | * | 2/1998 | McClure et al. | ............ 600/515 |
| 5,720,295 | A | * | 2/1998 | Greenhut et al. | ........... 600/517 |
| 5,730,144 | A | * | 3/1998 | Katz et al. | ................. 600/526 |
| 5,741,304 | A | * | 4/1998 | Patwardhan et al. | ........... 607/5 |
| 5,891,169 | A | * | 4/1999 | Boheim et al. | ................. 607/4 |
| 5,957,856 | A | * | 9/1999 | Weil et al. | .................. 600/518 |
| 6,112,117 | A | * | 8/2000 | KenKnight et al. | ............ 607/5 |

* cited by examiner

*Primary Examiner*—Jeffrey R. Jastrzab
(74) *Attorney, Agent, or Firm*—Porter, Wright, Morris & Arthur, LLP

(57) ABSTRACT

An apparatus for determining when a patient is susceptible to defibrillation comprises a plurality of electrodes (12, 14) for obtaining an ECG signal from a patient, and data processing means (30, 42) for determining a region of the ECG signal where the signal passes from a first threshold to a second threshold at least equal in magnitude but of opposite polarity to the first threshold while the gradient of the signal remains within certain limits, detecting the next following ECG signal peak, and providing an output signal upon such detection.

14 Claims, 15 Drawing Sheets

APPARATUS FOR DETERMINING WHEN A PATIENT IS SUSCEPTIBLE TO DEFIBRILLATION

Figure 1:
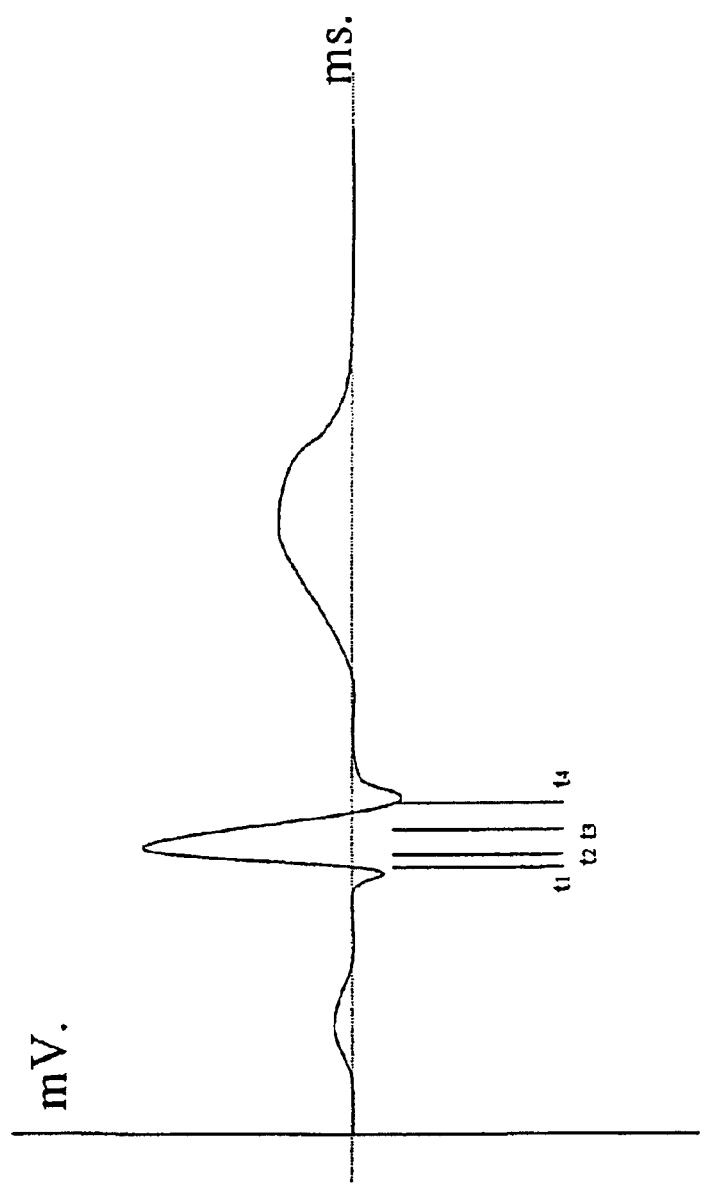

This invention relates to an apparatus for determining when a patient is susceptible to defibrillation.

Ventricular fibrillation (VF) is an abnormal rhythm of the heart which proves fatal if left untreated. The only effective treatment in an emergency situation is a high voltage shock applied to the heart either through electrodes applied to the chest wall or through electrodes attached directly onto the heart's surface. This high voltage shock attempts to interrupt the Ventricular fibrillation sequence and thereby restore the heart to a normal activation sequence.

A heart in VF is not effective and circulates very little blood, if any at all. A VF event is therefore probably the most time critical of all medical cases. With no blood circulation, brain tissue death or necrosis is imminent within minutes of the event occurring. The lack of blood supply to the body also compounds the time critical nature of the event because the heart itself requires blood supply via its coronary arteries in order to function efficiently. During VF with the blood supply to the whole body interrupted, the heart begins to experience ischaemia. Ischaemic heart tissue is more prone to VF than normal heart tissue. This means that as the VF rhythm persists, the ability to correct the sequence reduces and the risk of death increases.

There are various different mechanisms by which the Ventricular fibrillation sequence can maintain itself. Unlike Normal Sinus rhythm (a one shot sequence being actively initiated by the Sino-atrial Node), VF is a self sustaining closed loop sequence which is sometimes cyclic in nature but the nature of the sequence and its mechanism invariably changes over time. Furthermore, the mechanism by which any particular VF event is sustained will be related to the primary cause of the event. There are again various cardiac related abnormalities and trauma, which can promote a VF sequence in any human heart. These can be divided into two distinct groups, namely: Primary VF events and Secondary VF events.

Primary events are cases where the VF was an unexpected event. This can either be a sudden spontaneously initiated VF or a VF event due to some other sudden trauma or stress e.g. Acute Myocardial Infarction, Hypoxia, Lighting strike etc. Secondary events are those which occur although suddenly but predictably. These would include VF as a known risk of drug therapy and also patients who have a previous history of spontaneous VF events or rhythms which could promote VF. These two groups are managed differently by modern clinical response.

Secondary events are very well controlled by complex and miniaturised Implantable Cardiac Defibrillators (ICDs) which are surgically implanted within the chest and have electrodes directly connected to the heart. These devices continually monitor the hearts rhythm and deliver a shock to the heart if they detect the abnormal rhythm. Devices such as these have a very high success rate for converting VF since they can respond very quickly.

Primary events however are not so easily controlled. Due to the fact that by nature they are entirely unpredictable, they invariably occur outside hospital and therefore occur in the absence of specialised equipment and or qualified personnel. When they do occur, the response time may be long because an average person will fail to recognise the seriousness of the condition. This means that the event can neither be quickly diagnosed nor effectively treated. The advent of the Portable Cardiac Defibrillator was a significant advance for emergency response teams allowing them access to a very specialised medical instrument outside hospital. The procedure means that primary events can now be treated almost as successfully as secondary events provided the emergency response team can be despatched and reach the patient in time. This delay could be further reduced if the use of Automatic External Defibrillators (AED's) becomes more widespread.

Unfortunately, there is a dilemma associated with external defibrillation. Unlike ICDs, external defibrillators apply the electrical shock across the thorax rather than directly across the heart, requiring much larger voltages in order to deliver the energy to the heart, necessary for termination of the VF rhythm. As a result of this high voltage, very high currents can occur within the thoracic cage and cause significant damage to heart tissue. Clearly this is undesirable and defeats the purpose of the intended treatment. Furthermore, external defibrillation is probabilistic at best. For instance, having established an energy setting which has produced a successful defibrillation in one instance and then attempting to defibrillate with the same or higher energy setting may fail. Of even further interest is the fact that a significantly lower energy setting can be successful, all within the same individual.

For these reasons, low energy defibrillation has been a goal for investigators for many years. The object of the invention discussed here is not however that of low energy defibrillation but rather one of providing a means by which the probability of any defibrillation attempt being successful can be increased. It will become clear later however, that increasing the probability can mean that fewer lower amplitude shocks are actually required to terminate any given VF rhythm. Attempts to reduce the energy delivered to patients requiring defibrillation have evolved from recommended dose protocols, for example a first shock of 200J and if this is unsuccessful then a second shock of 200J and then repeated shocks of 360J until successful or the attempts are to be abandoned; to energy dose based upon patient characteristics, for example changing initial discharge voltage, initial current or the discharge pulse width in order to deliver less energy to patients with a lower Trans-Thoracic Impedance (TTI).

Although these types of refinement have advantages they do not increase the probability of defibrillation success and they can also have serious disadvantages. For example while decreasing the width of a shock pulse and keeping the initial discharge voltage constant for a low impedance patient means the subject receives a lower energy dose, the initial current flow through the subjects torso (and heart) is actually much greater and therefore very damaging.

Present theory projects that the state of the myocardium at the exact instant the shock is applied is actually the determining factor of a successful defibrillation attempt. Experiments changing the shape of the shock pulse itself have shown that different pulse shape characteristics can change the amount of energy required to terminate VF. It is widely accepted that although VF has a random appearance, it is characteristic and can in fact be successfully modelled.

Investigations in this field have shown that the success of a defibrillation attempt is governed by the ability of the applied shock pulse and its shape to successfully organise a critical mass of myocardial cells. Specifically, the critical mass of cells must be placed into the refractory (or recovery) state. If a critical mass can be organised in this way, the heart essentially pauses. The normal sinus pacemaker can then initiate the heart's normal activation sequence and normality is restored.

Recently however, investigators have shown that during VF the heart's organisational state changes over time, and specifically that there are instants during any VF sequence at which the heart is in a more organisational state. Attempts by various investigators to identify these instants (called periods or instants of defibrillation susceptibility) have only been marginally successful. In 1988 Carlisle et al. synchronised the applied shock to the peaks, troughs and zero crossing points of the ECG during VF, without any significant success.

The object of the invention is therefore to provide a means for determining when a patient is susceptible to defibrillation whereby the probability of any defibrillation attempt being successful can be increased.

Accordingly, the invention provides an apparatus for determining when a patient is susceptible to defibrillation, the system comprising a plurality of electrodes for obtaining an electrocardiographic (ECG) signal from a patient, and data processing means for (a) determining a region of the ECG signal where such signal passes from a first threshold to a second threshold at least equal in magnitude to that of the first threshold and of opposite polarity thereto while the gradient of such signal remains within certain limits, (b) detecting the next following ECG signal peak, and (c) providing an output signal upon such detection.

The invention further provides defibrillation apparatus in which the occurrence of the output signal is used to trigger the application of a defibrillation voltage across the defibrillation electrodes.

In such case the electrodes providing the ECG signal may be the defibrillation electrodes themselves.

The first and second thresholds and gradient limits may be calculated automatically from measured parameters of the preceding ECG signal, or they may be empirically determined constant values.

In the embodiment to be described the data processing means is implemented in digital circuitry. However, it may alternatively be implemented in analog circuitry or a combination of analog and digital circuitry.

Figure 2:
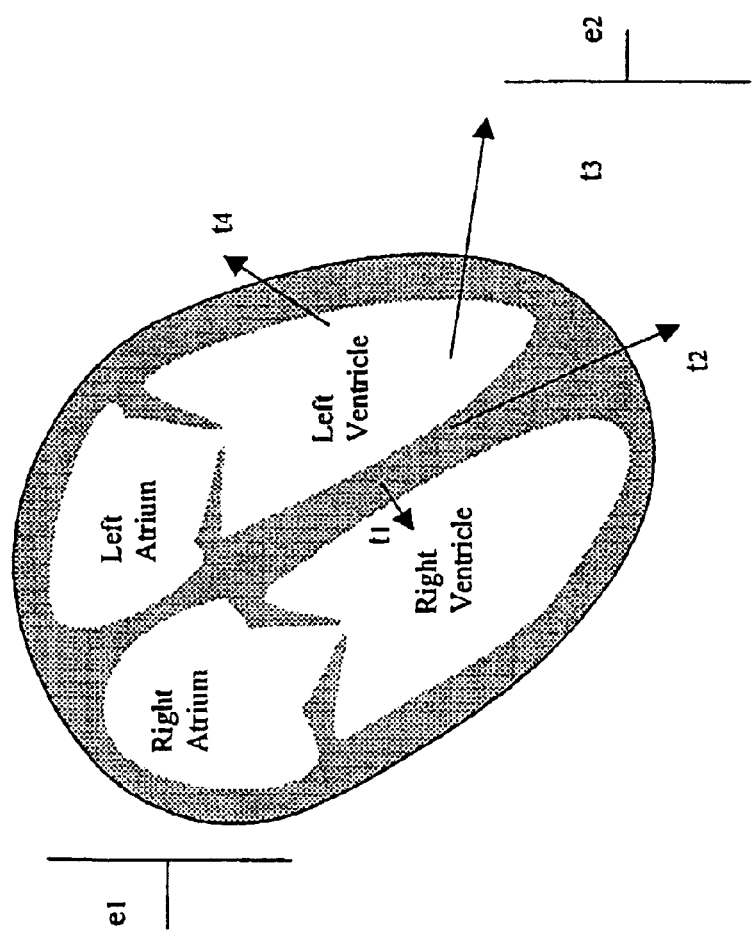
Figure 3:
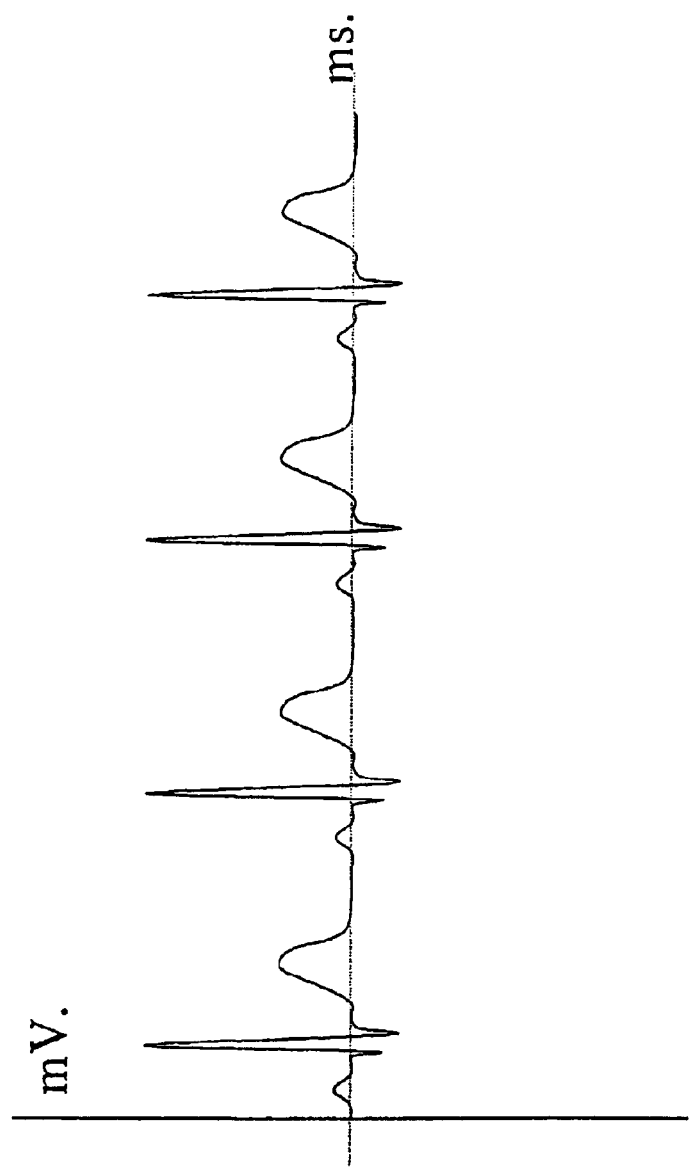
Figure 4:
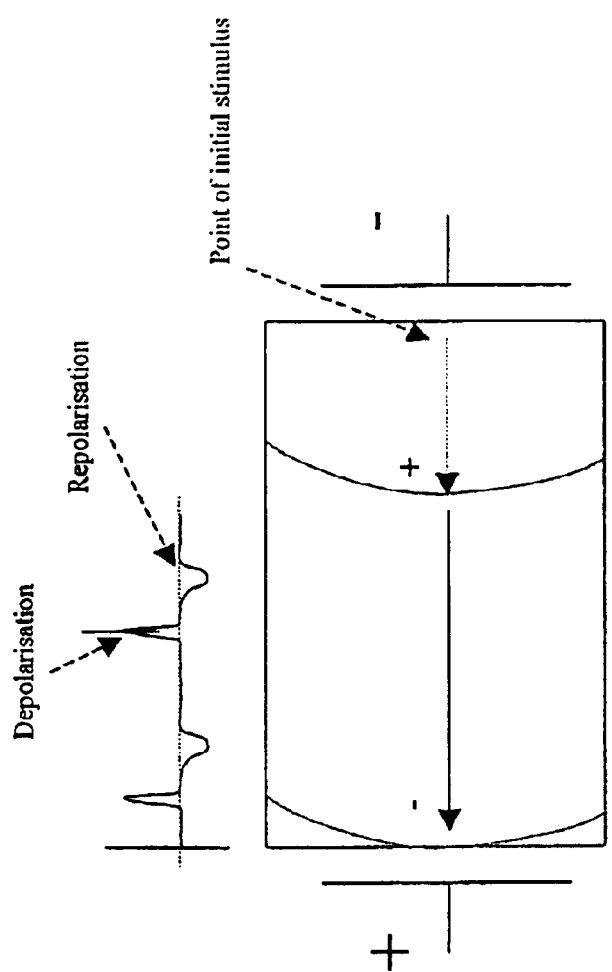
Figure 5:
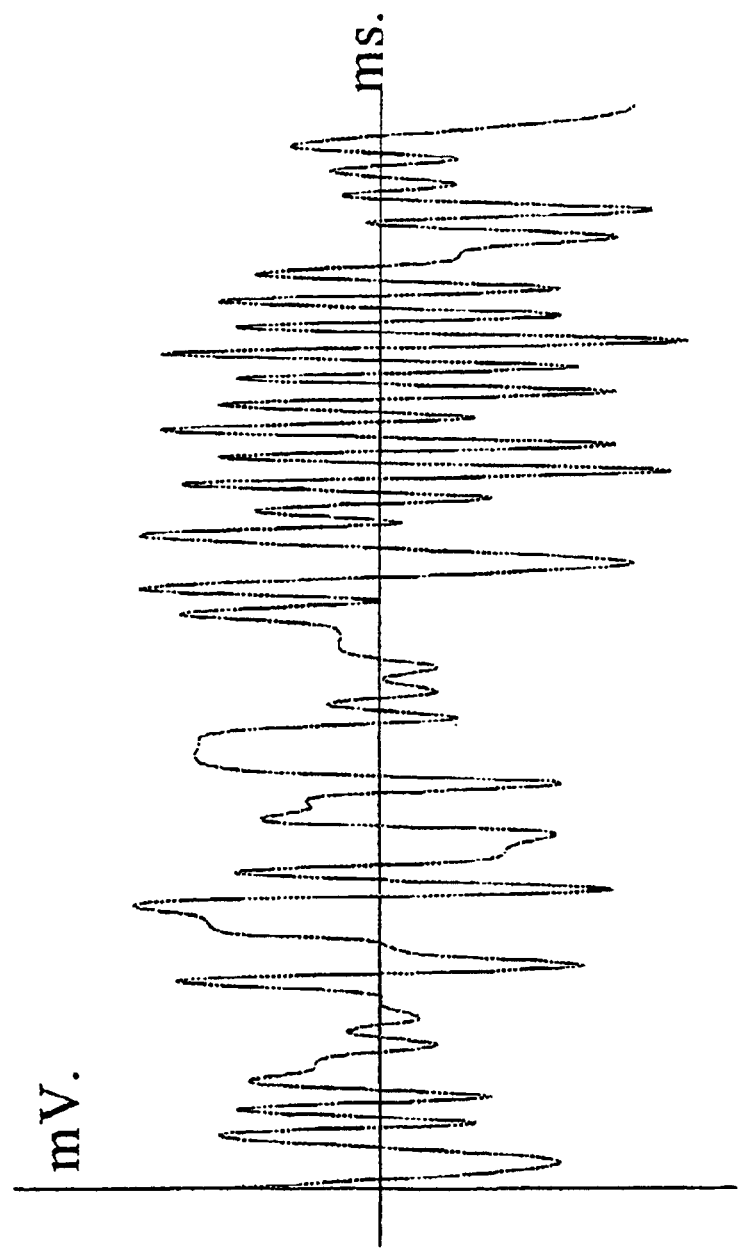
Figure 6:
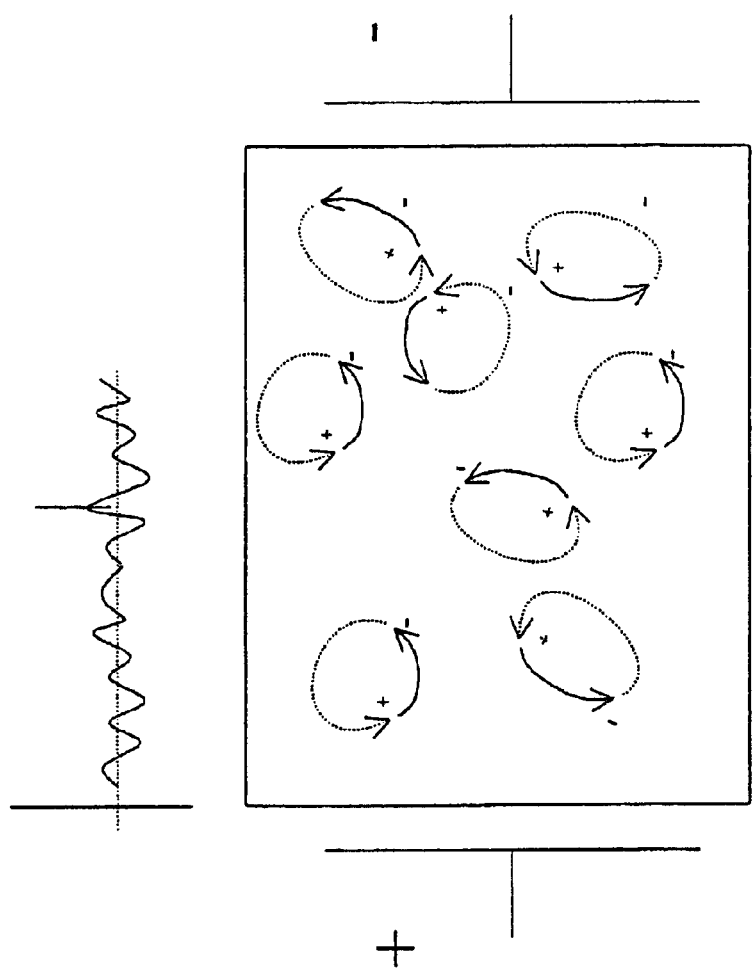
Figure 7:
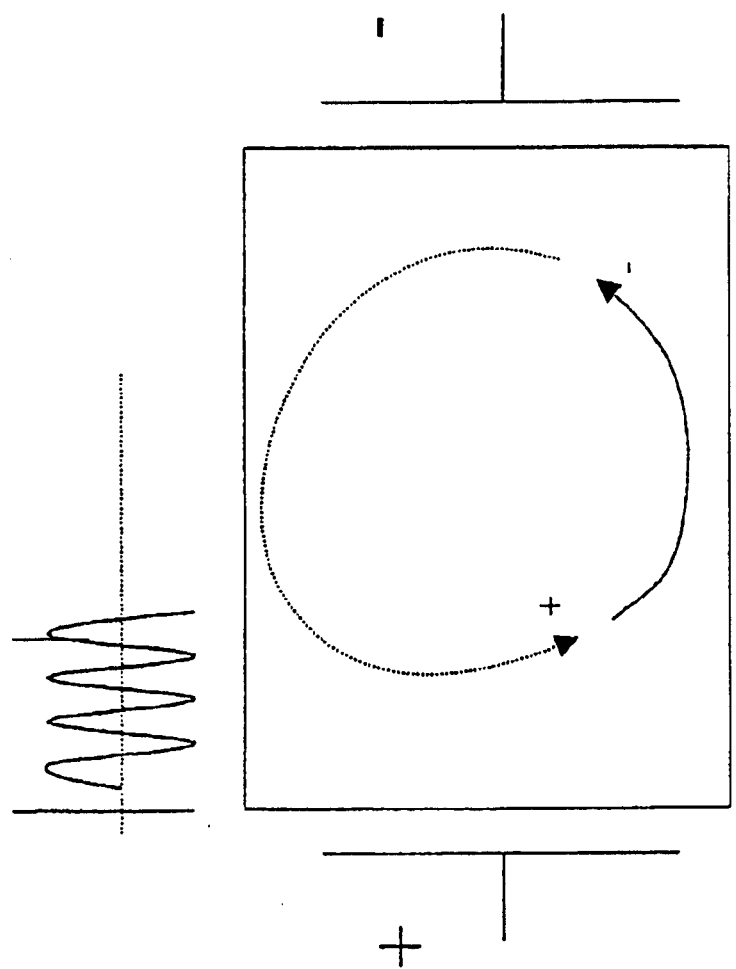
Figure 8:
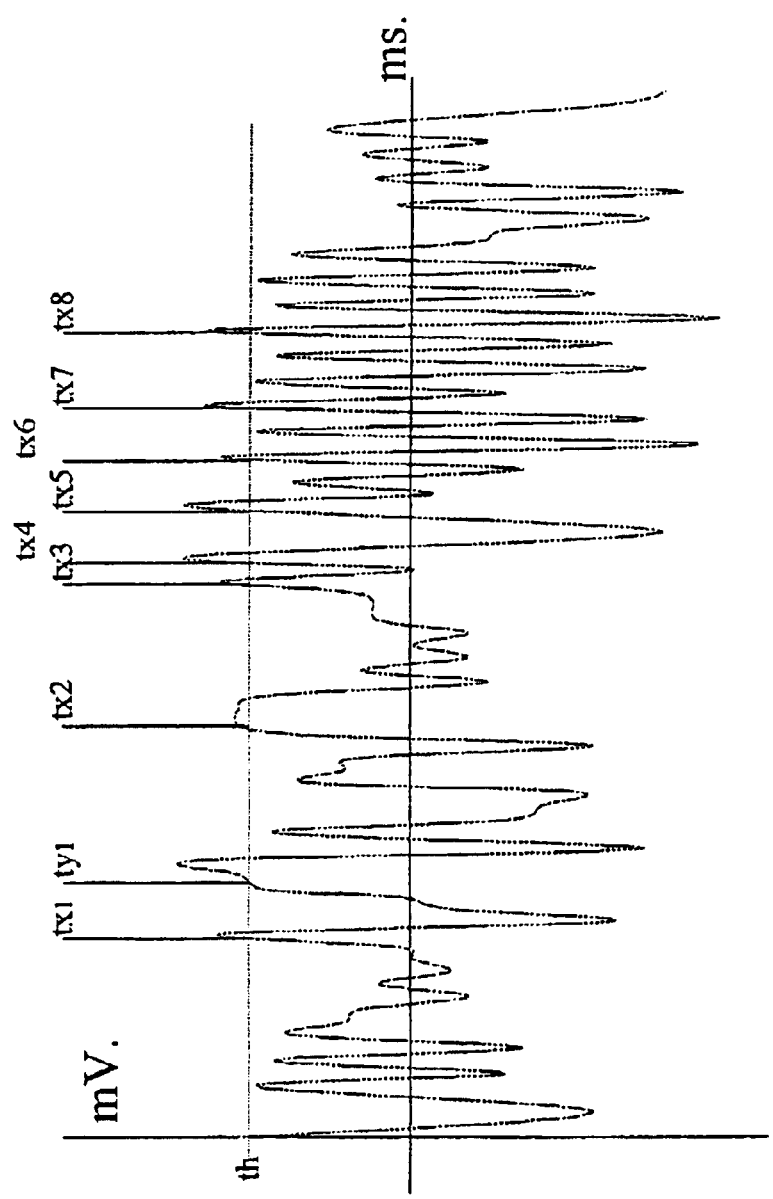
Figure 9:
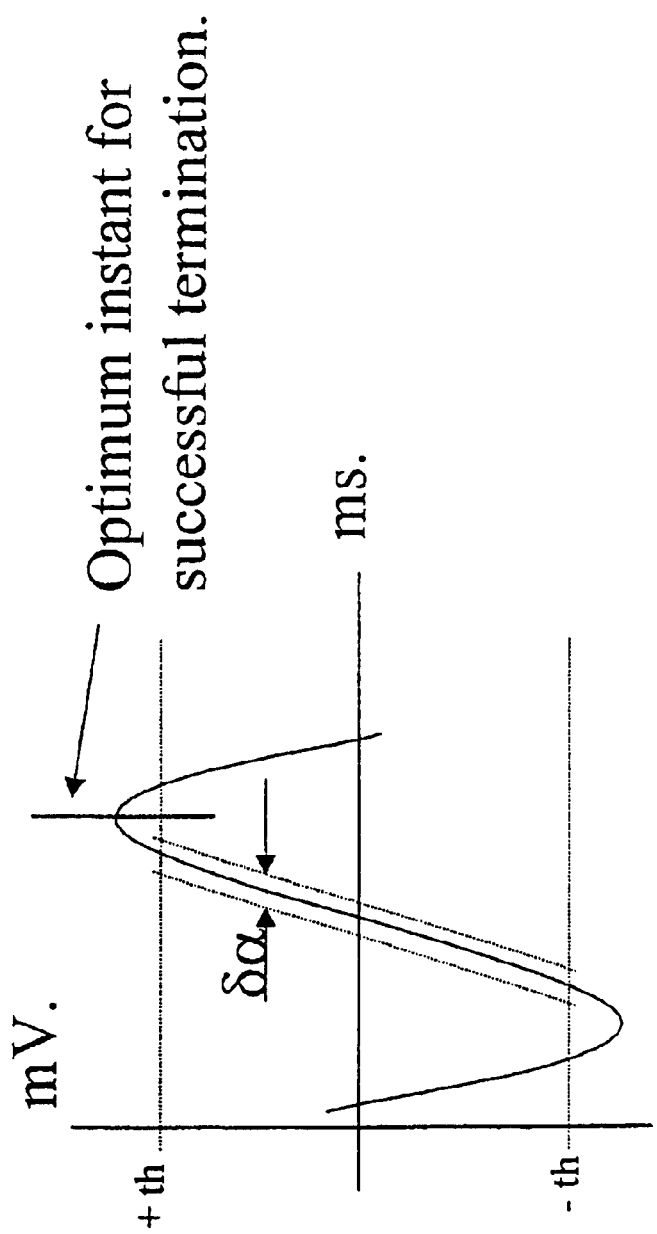
Figure 10:
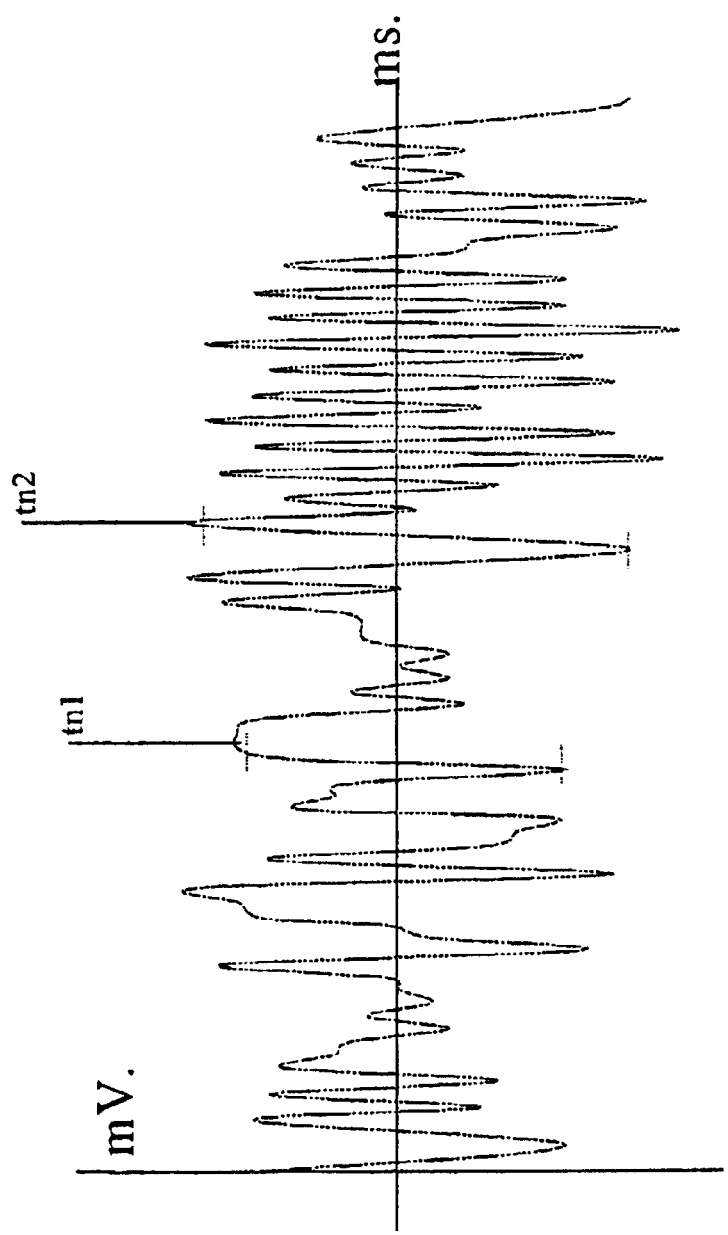
Figure 11:
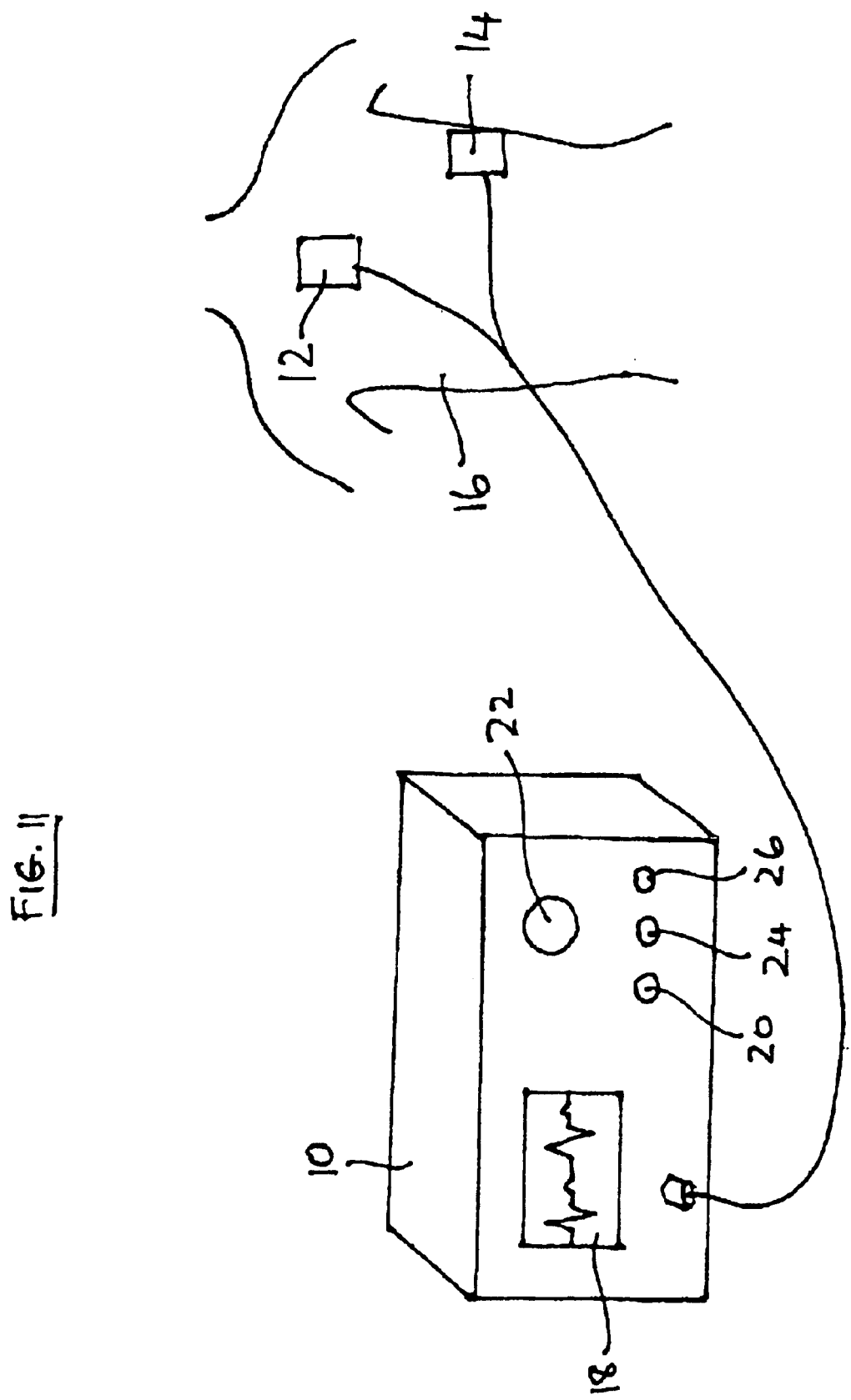
Figure 12:
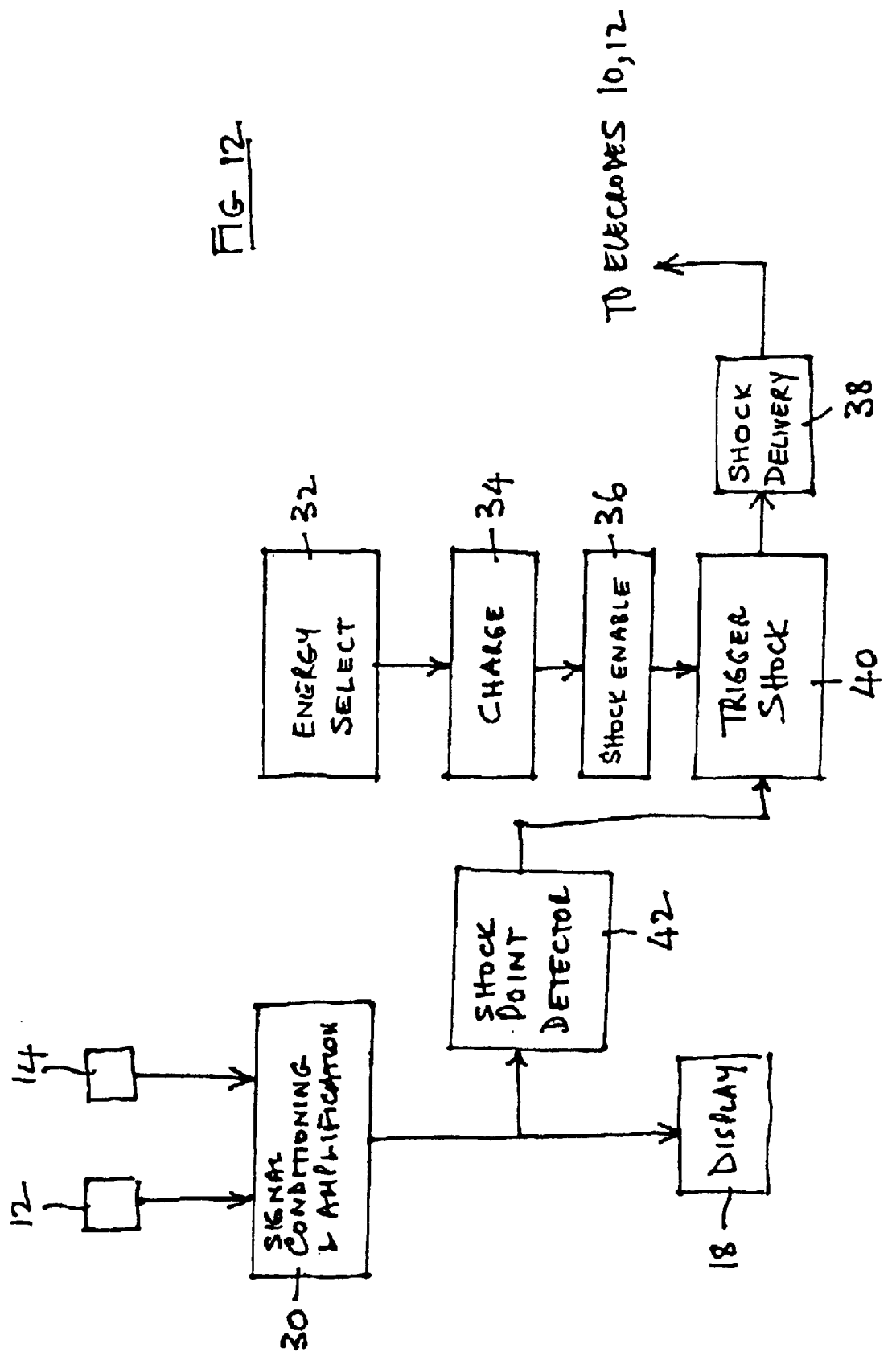
Figure 13:
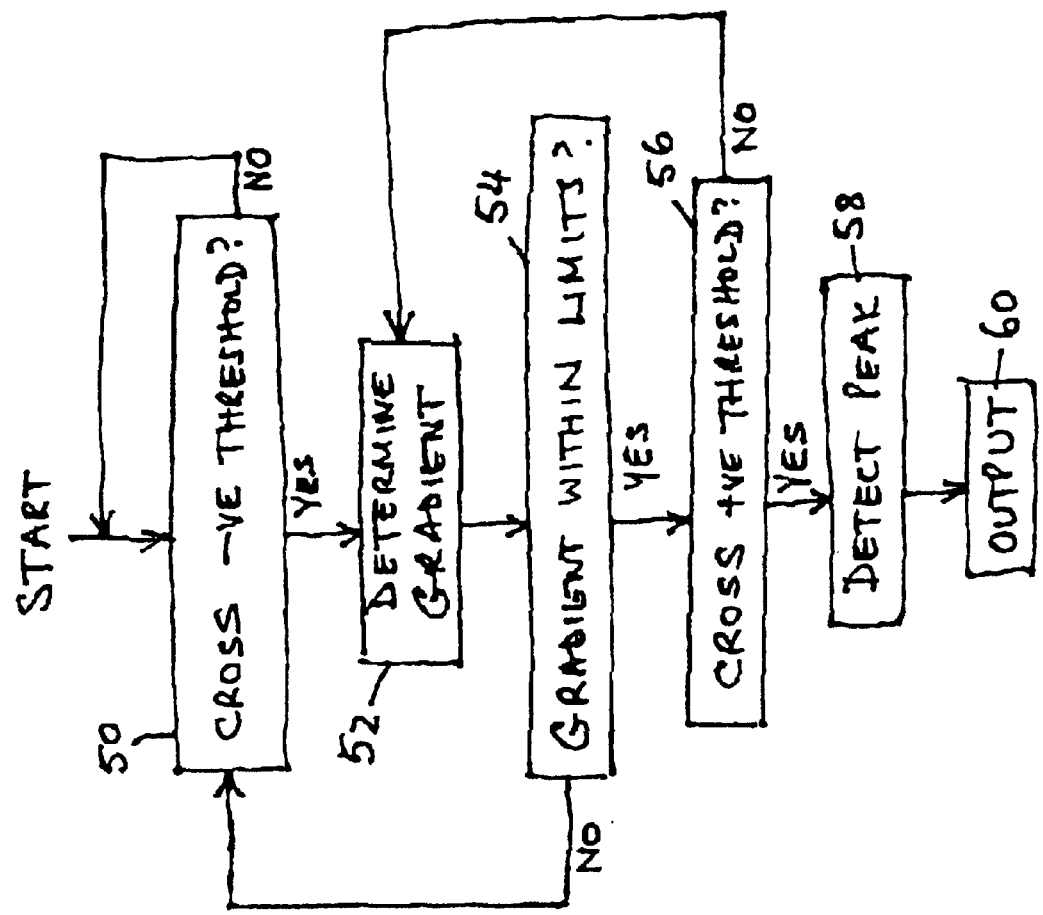
Figure 14:
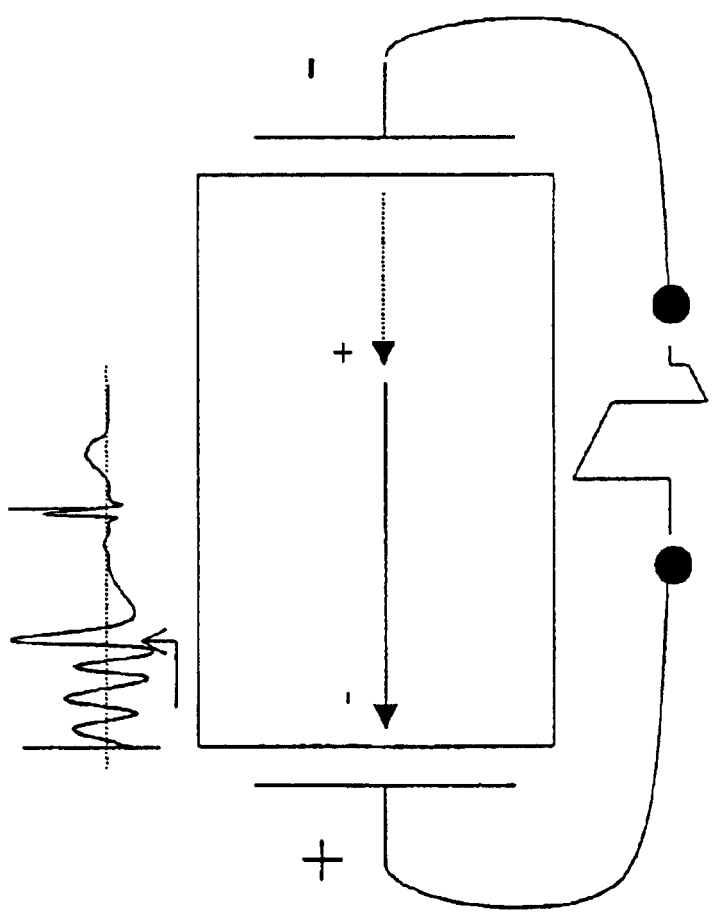
Figure 15:
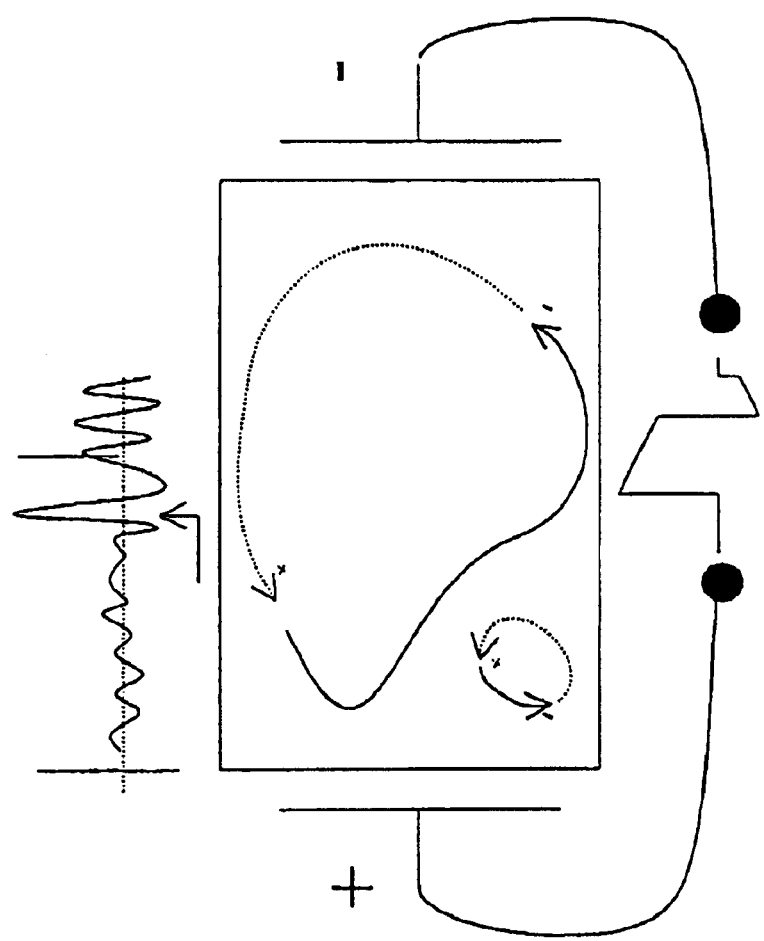

An embodiment of the invention will now be described, by way of example, with reference to the accompanying drawings, in which:

FIG. 1 shows a single bipolar lead ECG showing a normal sinus beat measured from the body surface, FIG. 2 is a diagram of a heart showing average cardiac vectors at four instants during a normal sinus beat corresponding to the ECG in FIG. 1, FIG. 3 shows normal sinus rhythm, FIG. 4 shows normal depolarisation and repolarisation of an isolated section of myocardium, FIG. 5 is a typical bipolar ECG trace showing VF, FIG. 6 shows a possible activation mechanism generating a VF ECG trace, FIG. 7 shows a single re-entrant activation loop, FIG. 8 shows the VF epoch of FIG. 5 with time markers showing the defibrillation points identified by the prior art, FIG. 9 illustrates the detection constraints imposed by the invention, FIG. 10 shows the VF epoch of FIG. 5 with time markers showing the points identified by the invention, FIG. 11 shows defibrillation apparatus embodying the invention, FIG. 12 is a functional block diagram of the internal circuitry of the apparatus of FIG. 11, FIG. 13 is a flow diagram of the operation of the shock point detector of FIG. 12, FIG. 14 is an example of the use of the invention to terminate a VF sequence through delivery of a biphasic electrical shock, and FIG. 15 is an example of the use of the invention terminating multiple re-entrant loops to form a dominant re-entrant loop.

The invention is based on the theory that the instants of susceptibility can be detected and quantified by the average cardiac vector but that the amplitude and velocity of the approaching dominant wavefront is insufficient to accurately determine the instant of susceptibility. The instantaneous direction of the dominant wavefront and the nature of the myocardial organisation responsible for this direction is crucial to identifying the exact instant of susceptibility.

FIG. 1 shows an ECG obtained from a heart in normal sinus rhythm. FIG. 2 shows a diagrammatic sketch of the heart with the average cardiac depolarisation vectors superimposed. Each vector is called an average vector because it depicts the sum of all the myocardial cells activated at that particular point in time. The vectors are numerically labelled to portray the time sequence and can be related to the ECG trace FIG. 1 in order to appreciate the myocardial organisation at any given time instant. Note that the placement of the electrodes e1 and e2 shown in FIG. 2 (which in this case are the defibrillation electrodes ultimately used to shock the heart) determines the shape of the acquired ECG so the organisational state of the heart at any given time instant as determined by any given ECG lead is with reference to the direction resolved by that particular lead. Note also that normal Sinus rhythm is a very stable sequence repeated in a controlled manner by the heart, FIG. 3 shows an example ECG lead trace for reference.

Further considering FIG. 1, it can be appreciated that as the heart activates the average cardiac vector changes position from that denoted by $t_1$, to $t_2$ then to $t_3$ and finally to $t_4$. Of particular interest here is that the ECG traces achieves maximum positive deflection between time instants $t_2$ and $t_3$. Referring now to FIG. 2 we see that between $t_2$ and $t_3$ the vector would be pointing in the direction of the axis between the two electrodes $e_1$ and $e_2$. It is a fundamental property of any bipolar ECG lead that when a depolarising myocardial wavefront is approaching along the axis of the lead, a maximum (positive) deflection will be measured and when it is retreating along the axis of the lead, a minimum (negative) deflection will be measured. Furthermore, if the wavefront is travelling in a direction perpendicular to the lead axis, no deflection (zero potential difference) will be measured. Before considering the properties of a VF sequence it must be appreciated that the ECG trace and the average cardiac vectors are a consequence of the activation wavefronts.

FIG. 4 shows how the activation of an isolated section of myocardium can be used to demonstrate a normal depolarisation and repolarisation sequence. Note that the average vectors are differentiated by a "−sign" for the depolarisation wave and a "+sign" for the repolarisation wave. Above the tissue section we can also see the electrical trace which this isolated activation would produce measured from the two electrodes positioned either side of the section. The measured ECG trace shows the sharper, faster depolarisation wave inscribing a positive deflection as it approaches the positive electrode, this is then followed by the slower repolarisation wave which inscribes a negative deflection. The repolarisation wave is negative because it is of the opposite polarity (positive rather than negative) as it approaches the positive electrode.

This particular activation sequence (with the repolarisation wave following behind the initial depolarisation wave) is typical of atrial tissue. Ventricular tissue actually repolarises in the opposite direction to which it initially depolarises. In terms of the measured ECG and FIG. 4 the only difference would be that for ventricular tissue, since the repolarisation wave would be receding away from the positive electrode it would actually inscribe a positive deflection in the ECG trace.

Now let us consider a VF trace and how myocardial tissue generates such a trace. FIG. 5 shows a typical epoch of VF. As we can see the trace does indeed appear random. This sequence is generated by tissue containing a varying number of wavefronts. FIG. 6 shows one possibility. Here we see that there are several wavefronts circulating without any apparent stimulus. These "loops" are self sustaining because the tissue is repolarising abnormally quickly so that the depolarising wavefront can actually reactivate the tissue rather than allowing the tissue to pause and wait for a normal stimulus. Note that since the individual wavefronts are completely independent, they will interfere so that the overall activation vector changes with time as presented by the ECG trace. Furthermore, in this particular example the "loops" are all the same diameter, this however would not necessarily be the case. It must now be appreciated that at any given time instant the wavefronts can be seen to be adding together more than at other times, resulting in a higher amplitude activation vector being measured externally. At other times the wavefronts could interfere more destructively causing lower amplitude activation vectors to be measured.

FIG. 7 shows another possibility. Here only one large wavefront is shown circulating around the entire tissue section. The nature of this particular tissue activation pattern is the most fundamental type of self-sustaining "or re-entrant" activation. This more basic type of abnormal activation is more descriptive of a Ventricular Tachycardia sequence. Note that as this single wavefront rotates, at any time instant there are large areas of the tissue section which be can be noted as either depolarised or repolarised. In fact at any time instant there will be almost one half of the tissue section depolarised and one half repolarised. If we now deliver an electric shock at a random time instant to the tissue section, it is clear why such a shock may only sometimes be successful. At the instant the shock is applied, the areas of tissue that are depolarised will be unaffected, the areas that are repolarised (and therefore ready for activation) will begin to depolarise. Since these areas are depolarised earlier as a result of the shock stimulus, they cannot now be activated again by the already present circulating wavefront. The activation sequence is therefore terminated by interruption of the reentrant loop. Note therefore that to successfully terminate such an abnormal sequence, the electrical shock should be delivered at any time instant where the result of the shock would be to cause a significant amount of the tissue mass to be depolarised so as to. interrupt the abnormal sequence. This implies that the electrical shock should be applied at any time instant where there is a significant amount of the tissue mass in a state of repolarisation.

If we now return to FIG. 6 and consider again how these individually circulating wavefronts interfere with each other over time, then we can see that the average cardiac vector and it's measurement (the ECG trace) is generated by the activation wavefronts combined. Note also that the act of measuring a threshold or a gradient at that threshold is not sufficient to determine the activation state of the tissue. Since the amplitude of the ECG trace is due to both the mass of tissue activation together with the direction in which it is activating they cannot be separated by a threshold. Furthermore the gradient only reveals the speed at which the overall wavefront is approaching or receding.

FIG. 8 shows time instant markers positioned at points along the trace of FIG. 5 where the prior art suggests susceptibility for defibrillation. It is the purpose of this invention to identify the optimum instant for susceptibility for interruption of a re-entrant loop by using the ECG trace to determine both from which direction the overall wavefront is coming and also in which direction it is going. This is achieved by noting a peak average cardiac vector of significant amplitude and then detecting an amplitude of like magnitude but of opposite polarity immediately following the first noted peak. Furthermore the form of the ECG trace between these instants of opposite polarity must be appreciably linear (that is to say of relatively uniform gradient). The average cardiac vector presents this property when the overall activation is due to a significantly sized activation wavefront travelling away from a point far from the positive sensing electrode to a point near to the same electrode. Upon detection of a wavefront with this property at the positive electrode, there will be a significant mass of tissue having just been depolarised and therefore emerging from recovery ready for activation. Note also that this tissue mass will be have been travelling in a direction towards the positive electrode, meaning that the intracellular current flow within the tissue will also be directed in that direction. The defibrillating shock should therefore be delivered immediately upon detection of this instant so that the sequence can be successfully interrupted.

Furthermore it is crucial that the polarity of the defibrillation shock is such that the critical mass of cells are depolarised and that the shock is not applied across the tissue in a direction attempting to reverse repolarisation. A reverse polarity shock would require more energy since it would have to both reverse repolarisation and then depolarise the critical mass, a process which is very unlikely since having attempted to reverse repolarisation, the critical mass of cells will be less likely to depolarise properly and the VF sequence would simply persist. Thus, as shown in FIG. 9 for a negative-to-positive going portion of the ECG signal, the object of the invention is to identify a region of the ECG signal where the signal passes from a negative threshold "−th" of significant magnitude to a positive threshold "+th" at least equal in magnitude to the negative threshold, while the gradient of the signal remains within certain limits. In FIG. 9, provided the signal stays within the "channel" defined by the notional inclined parallel dotted lines separated by the horizontal distance $\delta\alpha$, it is assumed that the gradient has remained within the required limits. Having detected such a region of the ECG signal, the optimum point for defibrillation is at the next following ECG signal peak, i.e. local maximum, at which the defibrillation shock should be delivered.

The invention is equally applicable to positive-to-negative-going portions of the ECG signal, in which case one would detect a region of the ECG signal where the signal passes from a positive threshold of significant magnitude to a negative threshold at least equal in magnitude to the positive threshold, while the gradient of the signal remains within certain limits, and the optimum point for defibrillation would be at the next following local minimum of the ECG signal FIG. 10 shows the previous epoch of VF from FIG. 5 but here the above technique has identified only the instants tn1 and tn2 which were truly susceptible to defibrillation. As mentioned previously, the upper and lower thresholds, indicated in FIG. 10 by the horizontal dashed lines, and the gradient limits may be calculated automatically from measured parameters of the preceding ECG signal, or they may be empirically determined constant values. In the case of FIG. 10 the thresholds are assumed to be a function of the average peak value of the preceding ECG signal.

An embodiment of the invention is shown in FIGS. 11 to 13 and is based upon a known type of external defibrillation apparatus. Since the modifications necessary to embody the invention are internal, the apparatus has the outward appearance (FIG. 11) of a conventional external defibrillation apparatus. Thus the apparatus includes a defibrillation unit 10 and a pair of defibrillation electrodes 12, 14 for application to a human torso 16, the electrodes being plugged into the unit 10. As well as being used to provide a defibrillation shock, the electrodes 12, 14 are also used as ECG electrodes to produce an ECG signal in known manner which is displayed on an ECG monitor 18 in the unit 10. A gain control knob 20 allows the amplitude of the signal trace to be adjusted on the monitor 18. The unit 16 also includes a rotary dial 22 to select the energy of the defibrillation shock to be applied to the patient, and a push button 24 which when pressed causes a capacitor inside the unit 16 to charge to a voltage determined by the setting of the selector 22. Finally, a further push button 26 is provided. In the conventional defibrillator an operator pushes this button to cause the capacitor to discharge through the electrodes 10, 12 to deliver a shock to the patient. However, in the present case the internal circuitry of the unit 16 is modified so that pushing the button 26 merely enables a shock to be given, the actual timing of the shock being determined according to the principles discussed above with reference to FIG. 9.

FIG. 12 is a block diagram of internal circuitry of the unit 10. The individual blocks shown in FIG. 12 identify the main functions of the unit, and do not necessarily constitute separate and distinct parts of the circuitry.

Signal Conditioning and Amplification circuit 30 receives the signals from the individual defibrillation electrodes 12, 14 and generates therefrom in known manner the ECG signal for display on the monitor 18. Energy Select circuit 32 is responsive to the setting of the rotary dial 22 to establish the selected energy level and, when the push button 24 is pressed, Charge circuit 34 charges the capacitor to a level corresponding to the selected energy level.

In the prior art, and as indicated by the dashed line, Shock Enable circuit 36 is directly responsive to the operator pressing the push button 26 to provide an input to Shock Delivery circuit 38, causing the latter to immediately discharge the capacitor through the electrodes 12, 14 to deliver a defibrillation shock to the patient. However, in the present embodiment the Shock Enable circuit 36 provides instead an input to Trigger Shock circuit 40 interposed between circuits 36 and 38. The Trigger Shock circuit 40 also receives an input from Shock Point Detector circuit 42 which is responsive to the ECG signal from circuit 30 to detect instants susceptible to defibrillation according to the principles of FIG. 9. The Shock Point Detector circuit 42 provides the said input to circuit 40 when such an instant is detected.

The Trigger Shock circuit 40 is essentially an AND circuit and, when it receives an input simultaneously from both circuits 36 and 42, it provides an input to the Shock Delivery Circuit 38 which causes the latter to immediately discharge the capacitor through the electrodes 12, 14 to deliver a defibrillation shock to the patient. Thus, as compared to the conventional external defibrillator which provides a defibrillation shock immediately the button 26 is pressed, which can occur at any arbitrary point during the ECG cycle due to the rapid changes in the signal and the relatively slow reaction of the human operator, in the present apparatus when the button 26 is pressed the apparatus waits until the Shock Point Detector circuit 42 identifies an instant susceptible to defibrillation and only then administers the shock. Such instant will typically occur a fraction of a second after the button 26 is pressed, and thus the button 26 must be held down until the shock is given. Optionally, if no suitable instant is detected within a predetermined time, say about two seconds, after the button 26 is pressed, the apparatus may be designed to administer a shock at that point anyway. The shock is preferably an n-phasic truncated exponential shock where n is greater than one. That is to say, it consists of several truncated exponential voltage pulses of alternating polarity. In particular it may be a biphasic truncated exponential shock.

The implementation of circuits 30 to 38 is well known in the art and does not need further description. Also, circuit 40 is essentially an AND circuit and is readily implemented by those skilled in the art. The function of the Shock Point Detector circuit 42 is performed in this embodiment by a suitably programmed microprocessor. In order to allow the microprocessor to process the ECG signal an analog-to-digital (A/D) converter (not shown) is used to convert the analog ECG signal to digital form.

FIG. 13 is a flow diagram of the program which is run on the microprocessor to identify the instants susceptible to defibrillation. The program starts when the push button 26 is pressed. Step 50 repeatedly tests the ECG signal to detect the ECG signal crossing a predetermined negative threshold in a positive-going direction, and when such a crossing is detected step 52 analyses the signal to determine its instantaneous gradient. Step 54 tests the gradient thus determined for being within predetermined limits. If the gradient is not within the limits, control passes back to step 50. If it is within limits, step 56 tests to determine if the signal has crossed a predetermined positive threshold at least equal in magnitude to that of the negative threshold. If it has, step 58 detects the next following peak (local maximum) and step 60 provides an output to the Trigger Shock circuit 40. If, however, step 56 determines that the signal has not crossed the positive threshold, control returns to step 52 and steps 52 to 56 are run through again. Thus, as time progresses from the crossing detection at step 50 the program repeatedly tests the gradient for being within limits, until either the signal crosses the positive threshold, in which case the next following peak is detected, or the gradient falls outside the limits, in which case control reverts to step 50 to look for the next crossing of the negative threshold.

FIG. 14 shows the invention having identified the correct instant of susceptibility and a biphasic truncated exponential shock was delivered to successfully terminate the VF event. The invention can also be used to terminate VF sequences sustained by multiple re-entrant loops as described above and shown in FIG. 6. In this instance the invention identifies the instant of greatest susceptibility and a first shock is delivered. FIG. 15 shows this process. As the figure shows, the purpose of the first shock is not to activate a critical mass and thereby terminate the VF sequence, but rather to just merge some of the small loops into one bigger loop. Successive shocks can therefore merge the loops into bigger and bigger loops until a final shock terminates the VF sequence.

The invention has been used to identify the instant of susceptibility in each case. This means that the energy required to defibrillate (either single shock or through multiple sequential shocks) is considerably less than would be required to activate a critical mass at a time instant that is not susceptible.

Although the above embodiment has used the same electrodes for both defibrillation and to provide the ECG signal which is analysed to determine the instant of susceptibility to defibrillation, the ECG signal could alternatively be derived from separate electrodes.

Also, although the foregoing has described the invention in the context of an external defibrillator, i.e. where the electrodes are connected externally to the patient's body, it will be clear to those skilled in the art that the invention may be used to determine the instant of susceptibility to defibrillation in the case of implanted electrodes which are connected directly to the heart's surface.

The invention is not limited to the embodiments described herein which may be modified or varied without departing from the scope of the invention.

What is claimed is:

1. An apparatus for determining an instant to apply a defibrillation voltage to a patient, the apparatus comprising a plurality of electrodes for obtaining an electrocardiographic (ECG) signal from a the patient, and data processing means for (a) determining a region of the ECG signal where such ECG signal passes from a first threshold to a second threshold at least equal in magnitude to that of the first threshold and of opposite polarity thereto while the gradient of such ECG signal remains within certain gradient limits, (b) detecting the next following ECG signal peak, and (c) providing an output signal upon such detection, wherein said output signal identifies the instant to apply the defibrillation voltage to the patient.

2. An apparatus as claimed in claim 1, wherein the first threshold is a negative threshold and the second threshold is a positive threshold.

3. An apparatus as claimed in claim 1, wherein the first threshold is a positive threshold and the second threshold is a negative threshold.

4. A defibrillator including an apparatus as claimed in claim 1, 2 or 3 wherein the occurrence of the output signal is used to trigger the application of a defibrillation voltage across defibrillation electrodes.

5. A defibrillator as claimed in claim 4, wherein the electrodes providing the ECG signal are also the defibrillation electrodes.

6. A defibrillator as claimed in claim 5, wherein the defibrillation voltage is an n-phasic truncated exponential voltage where n is greater than 1.

7. A defibrillator as claimed in claim 6, wherein the defibrillation voltage is a biphasic truncated exponential voltage.

8. A defibrillator as claimed in claim 5, wherein the defibrillation voltage is a biphasic truncated exponential voltage.

9. A defibrillator as claimed in claim 4, wherein the defibrillation voltage is an n-phasic truncated exponential voltage where n is greater than 1.

10. A defibrillator as claimed in claim 9, wherein the defibrillation voltage is a biphasic truncated exponential voltage.

11. A defibrillator as claimed in claim 4, wherein the defibrillation voltage is a biphasic truncated exponential voltage.

12. A defibrillator as claimed in claim 1, wherein the output signal is provided in real time upon detection of the next following ECG signal peak.

13. A method for determining an instant to apply a defibrillation voltage to a patient, the method comprising the steps of obtaining an electrocardiographic (ECG) signal from the patient using a plurality of electrodes, determining a region of the ECG signal where such ECG signal passes from a first threshold to a second threshold at least equal in magnitude to that of the first threshold and of opposite polarity thereto while the gradient of such ECG signal remains within certain gradient limits, detecting the next following ECG signal peak, providing an output signal upon such detection, and applying the defibrillation voltage to the patient upon the occurrence of said output signal.

14. The method as claimed in claim 13, wherein the step of providing the output signal is provided in real time upon the detection of the next following ECG signal peak.

* * * * *